United States Patent [19]

Cherpeck

[11] Patent Number: 5,482,522
[45] Date of Patent: Jan. 9, 1996

[54] MANNICH CONDENSATION PRODUCTS OF POLY(OXYALKYLENE) HYDROXYAROMATIC ESTERS AND FUEL COMPOSITIONS CONTAINING THE SAME

[75] Inventor: Richard E. Cherpeck, Cotati, Calif.

[73] Assignee: Chevron Chemical Company, San Ramon, Calif.

[21] Appl. No.: 175,700

[22] Filed: Dec. 30, 1993

[51] Int. Cl.$^6$ .................................................. C10L 1/18
[52] U.S. Cl. ................... 44/391; 44/399; 560/37; 560/50
[58] Field of Search .............................. 44/391, 399, 415, 44/385, 388, 389, 400, 405; 560/61, 63, 103, 37, 50

[56] References Cited

U.S. PATENT DOCUMENTS

| | | | |
|---|---|---|---|
| 3,285,855 | 11/1966 | Dexter et al. | 252/57 |
| 3,457,286 | 7/1969 | Dexter et al. | 44/399 |
| 3,849,085 | 11/1974 | Kreuz et al. | 44/78 |
| 3,944,594 | 3/1976 | Kleiner et al. | 44/389 |
| 3,980,569 | 9/1976 | Pindar et al. | 44/415 |
| 4,134,846 | 1/1979 | Machleder et al. | 252/51.5 A |
| 4,191,537 | 3/1980 | Lewis et al. | 44/71 |
| 4,231,759 | 11/1980 | Udelhofen et al. | 44/75 |
| 4,320,021 | 3/1982 | Lange | 252/51.5 R |
| 4,347,148 | 8/1982 | Davis | 252/51.5 R |
| 4,396,517 | 8/1983 | Gemmill, Jr. | 44/415 |
| 4,859,210 | 8/1989 | Franz et al. | 44/53 |
| 4,952,732 | 8/1990 | Speranza et al. | 564/390 |
| 5,196,142 | 3/1993 | Mollet et al. | 252/311 |

Primary Examiner—Margaret Medley
Attorney, Agent, or Firm—C. J. Caroli

[57] ABSTRACT

Mannich condensation products prepared by the condensation of a compound of the formula:

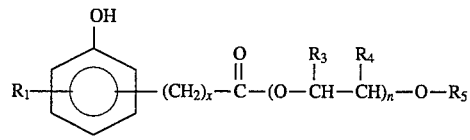

wherein $R_1$ is hydrogen, hydroxy, lower alkyl or lower alkoxy; $R_3$ and $R_4$ are independently hydrogen or lower alkyl; $R_5$ is hydrogen, alkyl, phenyl, aralkyl, alkaryl, or an acyl group of the formula:

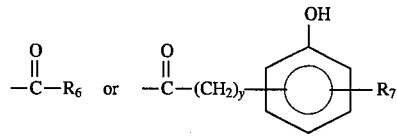

wherein $R_6$ is alkyl, phenyl, aralkyl or alkaryl; $R_7$ is hydrogen, hydroxy, lower alkyl or lower alkoxy; n is an integer from 5 to 100; and x and y are each independently an integer from 0 to 10;

with an aldehyde and a nitrogen base selected from ammonia, lower alkylamine, a polyamine and mixtures thereof.

The condensation products and their fuel soluble salts are useful as fuel additives for the prevention and control of engine deposits.

38 Claims, No Drawings

MANNICH CONDENSATION PRODUCTS OF POLY(OXYALKYLENE) HYDROXYAROMATIC ESTERS AND FUEL COMPOSITIONS CONTAINING THE SAME

BACKGROUND OF THE INVENTION

Field of the Invention

This invention relates to Mannich condensation products of certain poly(oxyalkylene) hydroxyaromatic esters. In a further aspect, this invention relates to the use of such compounds in fuel compositions to prevent and control engine deposits.

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to 0.25 volume percent of a high molecular weight aliphatic hydrocarbon-substituted phenol in which the aliphatic hydrocarbon radical has an average molecular weight in the range of about 500 to 3500. This patent teaches that gasoline compositions containing minor amounts of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Similarly, U.S. Pat. No. 4,134,846, issued Jan. 16, 1979 to Machleder et al., discloses a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Amino phenols are also known to function as detergents/ dispersants, antioxidants and anti-corrosion agents when used in fuel compositions. U.S. Pat. No. 4,320,021, issued Mar. 16, 1982 to R. M. Lange, for example, discloses amino phenols having at least one substantially saturated hydrocarbon-based substituent of at least 30 carbon atoms. The amino phenols of this patent are taught to impart useful and desirable properties to oil-based lubricants and normally liquid fuels.

Nitro phenols have also been employed as fuel additives. For example, U.S. Pat. No. 4,347,148, issued Aug. 31, 1982 to K. E. Davis, discloses nitro phenols containing at least one aliphatic substituent having at least about 40 carbon atoms. The nitro phenols of this patent are taught to be useful as detergents, dispersants, antioxidants and demulsifiers for lubricating oil and fuel compositions.

In addition, U.S. Pat. No. 4,231,759, issued Nov. 4, 1980 to Udelhofen et al., discloses a fuel additive composition comprising the Mannich condensation product of (1) a high molecular weight alkyl-substituted hydroxyaromatic compound wherein the alkyl group has a number average molecular weight of about 600 to about 3000, (2) an amine, and (3) an aldehyde. This patent teaches that such Mannich condensation products provide carburetor cleanliness when employed alone, and intake valve cleanliness when employed in combination with a hydrocarbon carrier fluid.

U.S. Pat. No. 4,859,210, issued Aug. 22, 1989 to Franz et al., discloses fuel compositions containing (1) one or more polybutyl or polyisobutyl alcohols wherein the polybutyl or polyisobutyl group has a number average molecular weight of 324 to 3000, or (2) a poly(alkoxylate) of the polybutyl or polyisobutyl alcohol, or (3) a carboxylate ester of the polybutyl or polyisobutyl alcohol. This patent further teaches that when the fuel composition contains an ester of a polybutyl or polyisobutyl alcohol, the ester-forming acid group may be derived from saturated or unsaturated, aliphatic or aromatic, acyclic or cyclic mono- or polycarboxylic acids.

U.S. Pat. No. 3,285,855, issued Nov. 15, 1966 to Dexter et al., discloses alkyl esters of dialkyl hydroxybenzoic and hydroxyphenylalkanoic acids wherein the ester moiety contains from 6 to 30 carbon atoms. This patent teaches that such esters are useful for stabilizing polypropylene and other organic material normally subject to oxidative deterioration. Similar alkyl esters containing hindered dialkyl hydroxyphenyl groups are disclosed in U.S. Pat. No. 5,196,565, which issued Mar. 23, 1993 to Ross.

U.S. Pat. No. 5,196,142, issued Mar. 23, 1993 to Mollet et al., discloses alkyl esters of hydroxyphenyl carboxylic acids wherein the ester moiety may contain up to 23 carbon atoms. This patent teaches that such compounds are useful as antioxidants for stabilizing emulsion-polymerized polymers.

Fuel additives containing a poly(oxyalkylene) moiety are also known in the art. For example, U.S. Pat. No. 4,191,537, issued Mar. 4, 1980 to R. A. Lewis et al., discloses a fuel composition comprising a major portion of hydrocarbons boiling in the gasoline range and from 30 to 2000 ppm of a hydrocarbyl poly(oxyalkylene) aminocarbamate having a molecular weight from about 600 to 10,000, and at least one basic nitrogen atom. The hydrocarbyl poly(oxyalkylene) moiety is composed of oxyalkylene units selected from 2 to 5 carbon oxyalkylene units. These fuel compositions are taught to maintain the cleanliness of intake systems without contributing to combustion chamber deposits.

Aromatic compounds containing a poly(oxyalkylene) moiety are also known in the art. For example, the above-mentioned U.S. Pat. No. 4,191,537, discloses alkylphenyl poly(oxyalkylene) polymers which are useful as intermediates in the preparation of alkylphenyl poly(oxyalkylene) aminocarbamates.

Additionally, hydroxyaromatic compounds containing a poly(oxyalkylene) moiety are known in the art. For example, U.S. Pat. No. 4,952,732, issued Aug. 28, 1990 to G. P. Speranza et al., discloses Mannich condensates prepared from a phenol, formaldehyde and an alkylamine containing propoxy groups and, optionally, ethoxy groups. These Mannich condensates are taught to be useful as corrosion inhibitors, water repellant agents, paint adhesion promotors, and also as intermediates for preparing surfactants, and pololys finding use in the manufacture of polyurethane foam.

My prior commonly assigned copending U.S. patent application Ser. No. 07/993,179, filed Dec. 18, 1992, discloses certain poly(oxyalkylene) hydroxyaromatic esters which provide excellent control of engine deposits, especially intake valve deposits, when employed as fuel additives in fuel compositions. These poly(oxyalkylene) hydroxyaromatic esters have been found to produce fewer combustion chamber deposits than known aliphatic hydrocarbon-substituted phenolic fuel additives.

SUMMARY OF THE INVENTION

It has now been discovered that certain Mannich condensation products of poly(oxyalkylene) hydroxyaromatic esters also provide excellent control of engine deposit, including intake valve deposits, with fewer combustion chamber deposit when employed as fuel additives, and further provide excellent control of injector deposits.

More specifically, the compounds of the present invention are Mannich condensation products prepared by the reaction of a poly(oxyalkylene) hydroxyaromatic ester of the formula:

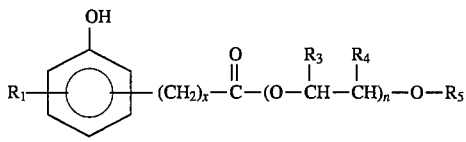

wherein $R_1$ is hydrogen, hydroxy, lower alkyl having 1 to 6 carbon atoms, or lower alkoxy having 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

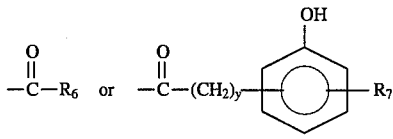

wherein $R_6$ is alkyl having 1 to 30 carbon atoms, phenyl, or aralkyl or alkaryl having 7 to 36 carbon atoms;

$R_7$ is hydrogen, hydroxy, lower alkyl having 1 to 6 carbon atoms, or lower alkoxy having 1 to 6 carbon atoms;

n is an integer from 5 to 100; and x and y are each independently an integer from 0 to 10;

with an aldehyde having the formula $HR_2C(O)$, wherein $R_2$ is hydrogen or lower alkyl having 1 to 6 carbon atoms, and a nitrogen base selected from ammonia, lower alkylamine having 1 to 6 carbon atoms, a polyamine having 2 to about 12 amine nitrogen atoms and 2 to about 40 carbon atoms and mixtures thereof.

Fuel soluble salts of the present Mannich condensation products are also contemplated and can be prepared by conventional procedures, for example, by reaction with an appropriate acid or base.

As is frequently the case with Mannich condensation products, the reaction product is typically a mixture of products because of competing or sequential reactions which result in secondary or derivative products, such as crosslinked products.

The amine moiety of the Mannich condensation product is preferably derived from a polyamine having from 2 to about 12 amine nitrogen atoms and from 2 to about 40 carbon atoms. The polyamine preferably has a carbon-to-nitrogen ratio of from about 1:1 to about 10:1. The polyamine may be substituted with substituents selected from hydrogen, hydrocarbyl groups of from 1 to about 10 carbon atoms, acyl groups of from 2 to about 10 carbon atoms, and monoketone, monohydroxy, mononitro, monocyano, alkyl and alkoxy derivatives of hydrocarbyl groups of from 1 to 10 carbon atoms. It is preferable that at least one of the basic nitrogen atoms of the polyamine is a primary or secondary amino nitrogen. The polyamine component employed in the present invention has been described and exemplified more fully in U.S. Pat. No. 4,191,537, the disclosure of which is incorporated by reference herein.

The base product and, in general, the principal Mannich condensation product of the invention can be represented by the formula:

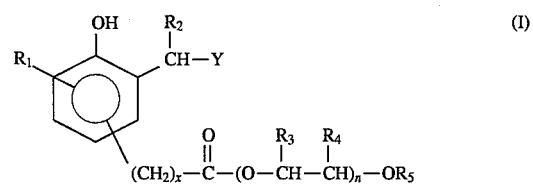

wherein $R_1$ is hydrogen, hydroxy, lower alkyl having 1 to 6 carbon atoms, or lower alkoxy having 1 to 6 carbon atoms;

$R_2$ is hydrogen or lower alkyl having 1 to 6 carbon atoms;

$R_3$ and $R_4$ are each independently hydrogen or lower alkyl having 1 to 6 carbon atoms;

R5 is hydrogen, alkyl having 1 to 30 carbon atoms, phenyl, aralkyl or alkaryl having 7 to 36 carbon atoms, or an acyl group having the formula:

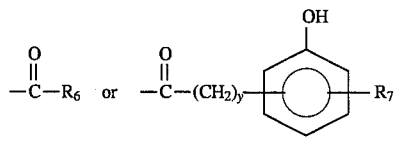

wherein $R_6$ is alkyl having 1 to 30 carbon atoms, phenyl, or aralkyl or alkaryl having 7 to 36 carbon atoms;

$R_7$ is hydrogen, hydroxy, lower alkyl having 1 to 6 carbon atoms, or lower alkoxy having 1 to 6 carbon atoms;

n is an integer from 5 to 100; and x and y are each independently an integer from 0 to 10;

Y is selected from amino, lower alkylamino having 1 through 6 carbon atoms or a polyamine radical, preferably a polyalkylene amine, having 2 through 12 amine nitrogen atoms and 2 through 40 carbon atoms, wherein the attachment of Y to the methylene linking group, i.e., —CH($R_2$)—, is through one of its amine nitrogen atoms. It is also understood that the —CHR$_2$—Y substituent is ortho to a hydroxy group on the aromatic ring and the remaining substituents may be at any available position on the aromatic ring.

In general, the commercial product will be a mixture of compounds according to formula I because, as noted above, the reaction product will be a mixture of products. In general, there is no commercial reason to isolate individual compounds. If desired, the individual compounds of formula I could be prepared by using individual compounds as starting materials and by isolating individual compounds from the product. But, as noted above, there is normally no commercial reason to isolate particular compounds when the product is used as a fuel additive and it generally would not be economical.

The present invention further provides a fuel composition comprising a major amount of hydrocarbons boiling in the gasoline or diesel range and an effective deposit-controlling amount of a compound or mixture of compounds of the present invention.

The present invention additionally provides a fuel concentrate comprising an inert stable oleophilic organic solvent boiling in the range of from about 150° F. to 400° F. and from about 10 to 70 weight percent of a compound or mixture of compounds of the present invention.

Among other factors, the present invention is based on the discovery that certain Mannich condensation products of poly(oxyalkylene) hydroxyaromatic esters are surprisingly useful for reducing engine deposits, especially on intake valves, when employed as fuel additives in fuel compositions.

DETAILED DESCRIPTION OF THE INVENTION

As noted above, because of competing or secondary reactions the Mannich condensation product of the present invention is typically a mixture of compounds. For example, where a long chain polyalkylene polyamine reactant is used, although the principal attachment of the polyamine radical to the benzyl ring will occur at the terminal nitrogen atoms, attachment can also occur at an internal amino nitrogen atom. Further, because of competing secondary reactions, cross-linked products are also produced. Thus, for example, in the case where diethylene triamine is the amine reactant, a significant amount of the bis product will also be produced, that is,:

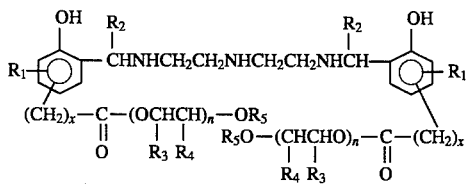

wherein $R_1$, $R_2$, $R_3$, $R_4$, $R_5$, x and n are as defined above.

The polyamine reactant used in the present invention is preferably an acyclic polyamine having terminal amino nitrogen atoms or less preferably a nitrogen heterocycle. In each case the amino nitrogen atoms are separated from each other by at least two carbon atoms. As noted above, the polyamine preferably has a carbon-to-nitrogen ratio of from about 1:1 to about 10:1. The polyamine may be substituted with substituents selected from hydrogen, hydrocarbyl groups of from 1 to about 10 carbon atoms, acyl grounds of from 2 to about 10 carbon atoms, and monoketone, monohydroxy, mononitro, monocyano, alkyl and alkoxy derivatives of hydrocarbyl groups of about from 1 to 10 carbon atoms. It is preferable that at least one of the basic nitrogen atoms of the polyamine is a primary or secondary amino nitrogen. The polyamine component employed in the present invention has been described and exemplified more fully in U.S. Pat. No. 4,191,537.

Hydrocarbyl, as used above, denotes an organic radical composed of carbon and hydrogen which may be aliphatic, alicyclic, aromatic or combinations thereof, e.g., aralkyl. Preferably, the hydrocarbyl group will be relatively free of aliphatic unsaturation, i.e., ethylenic and acetylenic, particularly acetylenic unsaturation. The substituted polyalkylene amines used in the present invention are generally, but not necessarily, N-substituted polyamines. Exemplary hydrocarbyl groups and substituted hydrocarbyl groups include alkyls such as methyl, ethyl, propyl, butyl, isobutyl, pentyl, hexyl, octyl, etc., alkenyls such as propenyl, isobutenyl, hexenyl, octenyl, etc., hydroxyalkyls, such as 2-hydroxyethyl, 3-hydroxypropyl, hydroxy-isopropyl, 4-hydroxybutyl, etc., ketoalkyls, such as 2-ketopropyl, 6-ketooctyl, etc., alkoxy and lower alkenoxy alkyls, such as ethoxyethyl, ethoxypropyl, propoxyethyl, propoxypropyl, diethyleneoxymethyl, triethyleneoxyethyl, tetraethyleneoxyethyl, diethyleneoxyhexyl, etc. The aforementioned acyl groups are such as propionyl, acetyl, etc. The more preferred substituents are hydrogen, $C_1$–$C_6$ alkyls and $C_1$–$C_6$ hydroxyalkyls.

In the substituted polyalkylene amine, the substituents are found at any atom capable of receiving them. The substituted atoms, e.g., substituted nitrogen atoms, are generally geometrically inequivalent, and consequently the substituted amines finding use in the present invention can be mixtures of mono- and poly-substituted polyamines with substituent groups situated at equivalent and/or inequivalent atoms.

Although, as noted above, a wide range of substituted and unsubstituted polyamines can be used, resulting in the corresponding Mannich condensation product, in general polyalkylene polyamines, including alkylene diamine, and including substituted polyalkyleneamines, e.g., alkyl and hydroxyalkyl-substituted polyalkylene polyamine are preferred. Preferably, the alkyl group linking the amino nitrogen groups contains from 2 to 6 carbon atoms, there being preferably from 2 to 3 carbon atoms between the nitrogen atoms. Such groups are exemplified by ethylene, 1,2-propylene, 2,2-dimethyl-propylene, trimethylene, 1,3,2-hydroxypropylene, etc. Examples of the polyalkylene amines from which such radicals are derived include ethylene diamine, diethylene triamine, di(trimethylene) triamine, dipropylene triamine, triethylene tetraamine, tripropylene tetraamine, tetraethylene pentamine, and pentaethylene hexamine. Such amines encompass isomers such as branched-chain polyamines and previously mentioned substituted polyamines, including hydroxy- and hydrocarbyl-substituted polyamines. Among the polyalkylene polyamines, those containing 2–12 amino nitrogen atoms and 2–24 carbon atoms are especially preferred, and the $C_2$–$C_3$ alkylene polyamines are most preferred, that is, ethylene diamine, polyethylene polyamine, propylene diamine and polypropylene polyamine, and in particular, the lower polyalkylene polyamines, e.g., ethylene diamine, dipropylene triamine, etc. A particularly preferred polyalkylene polyamine is diethylene triamine.

The amine component of the present fuel additive also may be derived from heterocyclic polyamines, heterocyclic substituted amines and substituted heterocyclic compounds, wherein the heterocycle comprises one or more 5–6 membered rings containing oxygen and/or nitrogen. Such heterocyclic rings may be saturated or unsaturated and substituted with groups selected from the aforementioned substituents. The heterocyclic compounds are exemplified by piperazines, such as 2-methylpiperazine, N-(2-hydroxyethyl)piperazine, 1,2-bis-(N-piperazinyl)ethane and N,N'-bis(N-piperazinyl)piperazine, 2-methyl-imidazoline, 3-amino-piperidine, 3-aminopyridine, N-(3-aminopropyl)-morpholine, etc. Among the heterocyclic compounds, the piperazines are preferred.

In terms of deposit control performance and/or manufacturing ease or blending facility, the preferred Mannich condensation products are, referring to the substituents identified in formula I and the corresponding fuel-soluble salts thereof, those having at least one of the following preferred substituents and more preferably two or more.

Preferably, $R_1$ is hydrogen, hydroxy, or lower alkyl having 1 to 4 carbon atoms. More preferably, $R_1$ is hydrogen or hydroxy. Most preferably, $R_1$ is hydrogen.

Preferably, Y is a radical derived from an unsubstituted polyalkylene polyamine, more preferably polyethylene polyamines or polypropylene polyamines.

$R_2$ is preferably hydrogen or lower alkyl having 1 to 4 carbon atoms. More preferably, $R_2$ is hydrogen.

Preferably, one of $R_3$ and $R_4$ is lower alkyl having 1 to 3 carbon atoms and the other is hydrogen. More preferably, one of $R_3$ and $R_4$ is methyl or ethyl and the other is hydrogen. Most preferably, one of $R_3$ and $R_4$ is ethyl and the other is hydrogen.

$R_5$ is preferably hydrogen, alkyl having 2 to 22 carbon atoms, or alkylphenyl having an alkyl group containing 2 to 24 carbon atoms. More preferably, $R_5$ is hydrogen, alkyl having 4 to 12 carbon atoms or alkylphenyl having an alkyl group containing 4 to 12 carbon atoms. Most preferably, $R_5$ is alkylphenyl having an alkyl group containing 4 to 12 carbon atoms.

$R_6$ is preferably alkyl having 4 to 12 carbon atoms.

Preferably, $R_7$ is hydrogen, hydroxy, or lower alkyl having 1 to 4 carbon atoms. More preferably, $R_7$ is hydrogen or hydroxy. Most preferably, $R_7$ is hydrogen.

$R_8$ is preferably hydrogen.

Preferably, n is an integer from 10 to 50. More preferably, n is an integer from 15 to 30. Preferably, x is an integer from 0 to 2. More preferably, x is 0. Preferably, y is an integer from 0 to 2. More preferably, y is 0.

A preferred group of Mannich condensation products are those of formula I wherein $R_1$ is hydrogen, hydroxy, or lower alkyl having 1 to 4 carbon atoms; $R_2$ is hydrogen; one of $R_3$ and $R_4$ is hydrogen and the other is methyl or ethyl; $R_5$ is hydrogen, alkyl having 2 to about 22 carbon atoms or alkylphenyl having an alkyl group containing 4 to about 24 carbon atoms; n is 15 to 30 and x is 0; and Y is a polyethylene polyamine radical.

Another preferred group of Mannich condensation products are those of formula I wherein $R_1$ is hydrogen, hydroxy, or lower alkyl having 1 to 4 carbon atoms; $R_2$ is hydrogen; one of $R_3$ and $R_4$ is hydrogen and the other is methyl or ethyl; $R_5$ is hydrogen, alkyl having 2 to about 22 carbon atoms or alkylphenyl having an alkyl group containing 4 to about 24 carbon atoms; n is 15 to 30; x is 1 or 2; and Y is a polyethylene polyamine radical.

A more preferred group of Mannich condensation products are those of formula I wherein $R_1$ is hydrogen or hydroxy; $R_2$ is hydrogen; one of $R_3$ and $R_4$ is hydrogen and the other is methyl or ethyl; $R_5$ is hydrogen, alkyl having 4 to 12 carbon atoms or alkylphenyl having an alkyl group containing 4 to 12 carbon atoms; n is 15 to 30; x is 0; and Y is an ethylene diamine or diethylene triamine radical.

It is especially preferred that the aromatic hydroxyl group or groups present in the compounds of formula I, above, be situated in a meta or para position relative to the poly(oxyalkylene) ester moiety.

Generally, the poly(oxyalkylene) hydroxyaromatic esters of this invention will contain an average of about 5 to about 100 oxyalkylene units; preferably, 10 to 50 oxyalkylene units; more preferably, 15 to 30 oxyalkylene units.

Preferably, the compounds of the present invention will have a sufficient molecular weight so as to be non-volatile at normal engine intake valve operating temperatures (about 200°–250° C.). Typically, the average molecular weight of the primary or monomeric reaction product, i.e., the compounds of formula I, will range from about 550 to about 6000. More preferably, the compound and salts have an average molecular weight of about from 600 to 4000, more preferably from 700 to 3000. Generally average molecular weight will primarily be a function of the poly(oxyalkylene) ester substituent but can also be influenced by the chain length of the polyamine substituent. The molecular weight of the product mixture will also be affected by cross-linking. Thus, the primary considerations are volatility and fuel solubility and not the technical molecular weight of the product mixture.

Fuel soluble salts of the Mannich condensation products are also useful for preventing or controlling engine deposits and, in some cases, may improve solubility. Suitable salts include, for example, those obtained by protonating the amino moiety with an acid or deprotonating the phenol moiety with a base. Preferred salts are derived from toluenesulfonic acid and methanesulfonic acid or are alkali metal and substituted ammonium salts.

Definitions

As used herein, the following terms have the following meanings unless expressly stated to the contrary.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "lower alkoxy" refers to the group —$OR_a$ wherein $R_a$ is lower alkyl. Typical lower alkoxy groups include methoxy, ethoxy, and the like.

The term "alkaryl" refers to the group:

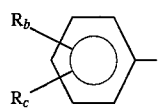

wherein $R_b$ and $R_c$ are each independently hydrogen or an alkyl group, with the proviso that both $R_b$ and $R_c$ are not hydrogen. Typical alkaryl groups include, for example, tolyl, xylyl, cumenyl, ethylphenyl, butylphenyl, dibutylphenyl, hexylphenyl, octylphenyl, dioctylphenyl, nonylphenyl, decylphenyl, didecylphenyl, dodecylphenyl, hexadecylphenyl, octadecylphenyl, icosylphenyl, tricontylphenyl and the like. The term "alkylphenyl" refers to an alkaryl group of the above formula in which $R_b$ is alkyl and $R_c$ is hydrogen.

The term "aralkyl" refers to the group:

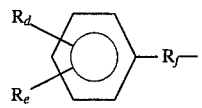

wherein $R_d$ and $R_e$ are each independently hydrogen or an alkyl group; and $R_f$ is an alkylene group. Typical alkaryl groups include, for example, benzyl, methylbenzyl, dimethylbenzyl, phenethyl, and the like.

The term "oxyalkylene unit" refers to an ether moiety having the general formula:

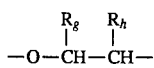

wherein $R_g$ and $R_h$ are each independently hydrogen or lower alkyl groups.

The term "poly(oxyalkylene)" refers to a polymer or oligomer having the general formula:

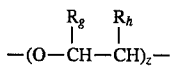

wherein $R_g$ and $R_h$ are as defined above, and z is an integer greater than 1. When referring herein to the number of poly(oxyalkylene) units in a particular poly(oxyalkylene) compound, it is to be understood that this number refers to the average number of poly(oxyalkylene) units in such compounds unless expressly stated to the contrary.

The term "polyamine" as used herein refers to polyamines containing 2 to 12 amine nitrogen atoms and 2 to 40 carbon atoms and includes both acyclic and cyclic polyamines and may be substituted with a variety of substituents so long as the substitution does not significantly adversely affect the deposit control and fuel compatibility properties of the present compositions.

The term "polyalkylene amine" by definition contains at least two amine groups; e.g., $NH_2$-alkylene-$NH_2$.

The term "fuel" refers to liquid hydrocarbon compounds such as petroleum fuels or synthetic fuels which are useful as fuels in spark ignition or combustion fire engines and may also contain minor amounts of other auxiliary fuels.

The term "engine" refers to internal combustion engines and includes both spark ignition engines and combustion fired engines such as diesel engines.

SYNTHESIS

The compounds of formula I can be conveniently prepared by the following schematically represented process:

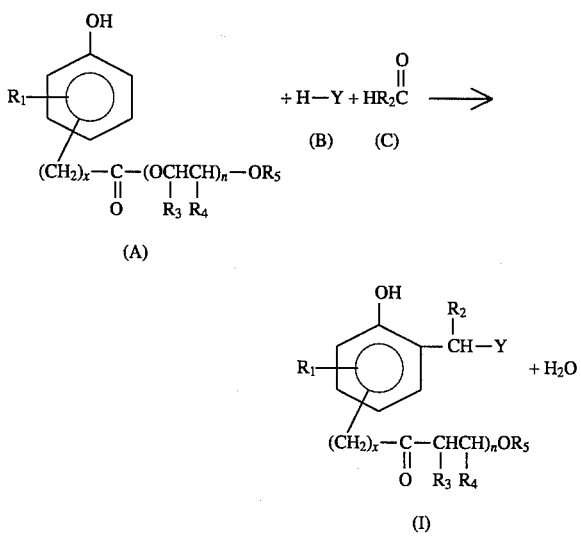

wherein $R_1$, $R_2$, $R_3$, $R_4$, $R_5$, Y, n and x are as defined hereinabove.

This process can be conducted by contacting reactants (A), (B) and (C) under reactive conditions, optionally in an inert solvent or liquid reaction medium. Typically, the reaction is conducted at temperatures in the range of about from 25° C. to 200° C., preferably 75° C. to 150° C. for about from 1 to 50 hours, preferably 5 to 20 hours using mole ratios of reactant in the range of about from 0.1 to 10, preferably 0.3 to 3 moles of reactant (B) and 0.1 to 10, preferably 1 to 5 moles of aldehyde (C) per mole of A. Suitable inert organic solvents or liquid diluents (reaction medium) which can be used include, for example, toluene, xylene, chloroform, acetonitrile, and the like and compatible mixtures thereof. Again, although the reaction product is shown for convenience as formula (I) the condensation product will generally be a mixture of products reflecting competing and secondary reaction products; such as, for example, further reactions or cross-linking of amino nitrogens in the polyalkylene amine substituent.

Reactant (B) is the compound form corresponding to the radical Y and includes ammonia, lower alkyl amine (for example, methylamine, isopropylamine, hexylamine) and polyamines as defined hereinabove. The polyamine must contain at least one primary or secondary amino group because the reaction proceeds by displacement of one of the amino hydrogen groups. Suitable substituted and unsubstituted polyalkylene amines which can be used in the aforedescribed process include, for example, ethylene diamine, 1,2-propylene diamine, 1,3-propylene diamine, diethylene triamine, triethylene tetraamine, hexamethylene diamine, tetraethylene pentamine, dimethylaminopropylene diamine, N-(beta-aminoethyl)piperazine, N-(beta-aminoethyl) morpholine, N,N'-di(beta-aminoethyl)piperazine, N,N'-di(beta-aminoethyl)imidazolidone, N-(beta-cyanoethyl) ethane-1,2-diamine, 1-amino-3,6,9-triazaoctadecane, 1-amino-3,6-diaza-9-oxadecane, N-(beta-aminoethyl) diethanolamine, N'-acetylmethyl-N-(beta-aminoethyl) ethane-1,2-diamine, N-acetonyl-1,2-propanediamine, N-(beta-nitroethyl)-1,3-propane diamine, 1,3-dimethyl-5-(beta-aminoethyl)hexahydrotriazine, N-(beta-aminoethyl)hexahydrotriazine, 5-(beta-aminoethyl)-1,3,5-dioxazine, 2-(2-aminoethylamino)ethanol, and 2-[2-(2-aminoethylamino) ethylamino]ethanol, and the like. Again, because the commercially produced polyalkylene amines are in many instances mixtures of polyalkylene amine, it is convenient to use the commercial mixture and correspondingly the product of formula I will also be a mixture.

The commercial polyalkylamines are typically mixtures in which one or several compounds predominate with the average composition indicated. For example, tetraethylene pentamine prepared by the polymerization of aziridine or the reaction of dichoroethylene and ammonia will have both lower and higher amine members, e.g., triethylene tetraamine, substituted piperazines and pentaethylene hexamine, but the composition will be mainly tetraethylene pentamine and the empirical formula of the total amine composition will closely approximate that of tetraethylene pentamine. Finally, in preparing the compounds of this invention, where the various nitrogen atoms of the polyamine are not geometrically equivalent, several substitutional isomers are possible and are encompassed within the final product.

The above-described amines are generally known compounds and, as noted above, are, in many cases, commercial commodities and in any case can be prepared by known procedures or obvious modifications thereof, e.g., substitution of appropriate starting materials and optimization of reaction conditions.

Methods of preparation of amines and their reactions are detailed in Sidgewick's "The Organic Chemistry of Nitrogen", Clarendon Press, Oxford, 1966; Noller's "Chemistry of Organic Compounds", Saunders, Philadelphia, 2nd Ed., 1957; and Kirk-Othmer's "Encyclopedia of Chemical Technology", 2nd Ed., especially Volume 2, pp. 99–116.

The compounds of formula A, above, may be prepared by the procedures described in my commonly assigned copending U.S. patent application Ser. No. 07/993,179, filed Dec. 18, 1992, the disclosure of which is hereby incorporated by reference herein in its entirety.

In accordance with the procedures described in U.S. Ser. No. 07/993,179, the poly(oxyalkylene) hydroxyaromatic esters of formula A may be prepared by the following general methods and procedures. It should be appreciated that where typical or preferred process conditions (e.g. reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

The poly(oxyalkylene) hydroxyaromatic esters of formula A having the formula:

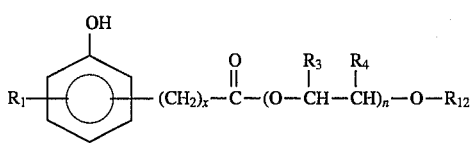

(III)

wherein $R_1$, $R_3$, $R_4$, n and x are as defined above and $R_{12}$ is an alkyl, phenyl, aralkyl or alkaryl group, may be prepared by esterifying a hydroxyaromatic carboxylic acid having the formula:

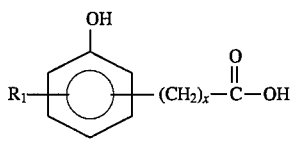

(IV)

wherein $R_1$ and x are as defined above, with a poly(oxyalkylene) alcohol having the formula:

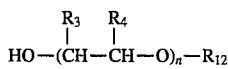

(V)

wherein $R_3$, $R_4$, $R_{12}$ and n are as defined above, using conventional esterification reaction conditions.

The hydroxyaromatic carboxylic acids of formula IV are either known compounds or can be prepared from known compounds by conventional procedures. Suitable hydroxyaromatic carboxylic acids for use as starting materials in this invention are 2-hydroxybenzoic acid, 3-hydroxybenzoic acid, 4-hydroxybenzoic acid, 3,4-dihydroxybenzoic acid, 3,4,5-trihydroxybenzoic acid, 3-hydroxy-4-methoxybenzoic acid, 4-hydroxy-3-methoxybenzoic acid, 3-t-butyl-4-hydroxybenzoic acid, 3,5-di-t-butyl-4-hydroxybenzoic acid, 4-hydroxyacetic acid, 3-(4-hydroxyphenyl)propionic acid, and the like.

The poly(oxyalkylene) alcohols of formula V may also be prepared by conventional procedures known in the art. Such procedures are taught, for example, in U.S. Pat. Nos. 2,782,240 and 2,841,479, which are incorporated herein by reference.

Preferably, the poly(oxyalkylene) alcohols of formula V are prepared by contacting an alkoxide or phenoxide metal salt having the formula:

$$R_{12}OM$$ (VI)

wherein $R_{12}$ is as defined above and M is a metal cation, such as lithium, sodium, or potassium, with about 5 to about 100 molar equivalents of an alkylene oxide (an epoxide) having the formula:

(VII)

wherein $R_3$ and $R_4$ are as defined above.

Generally, metal salt VI is prepared by contacting the corresponding hydroxy compound $R_{12}OH$ with a strong base, such as sodium hydride, potassium hydride, sodium amide and the like, in an inert solvent, such as toluene, xylene and the like, under substantially anhydrous conditions at a temperature in the range from about −10° C. to about 120° C. for about 0.25 to about 3 hours.

Metal salt VI is generally not isolated, but is reacted in situ with the alkylene oxide VII to provide, after neutralization, the poly(oxyalkylene) alcohol V. This polymerization reaction is typically conducted in a substantially anhydrous inert solvent at a temperature of about 30° C. to about 150° C. for about 2 to about 120 hours. Suitable solvents for this reaction, include toluene, xylene and the like. The reaction will generally be conducted at a pressure sufficient to contain the reactants and the solvent, preferably at atmospheric or ambient pressure.

The amount of alkylene oxide employed in this reaction will depend on the number of oxyalkylene units desired in the product. Typically, the molar ratio of alkylene oxide VII to metal salt VI will range from about 5:1 to about 100:1; preferably, from 10:1 to 50:1, more preferably from 15:1 to 30:1.

Suitable alkylene oxides for use in the polymerization reaction include, for example, ethylene oxide; propylene oxide; butylene oxides, such as 1,2-butylene oxide (1,2-epoxybutane) and 2,3-butylene oxide (2,3-epoxybutane); pentylene oxides; hexylene oxides; octylene oxides and the like. Preferred alkylene oxides are propylene oxide and 1,2-butylene oxide.

In the polymerization reaction, a single type of alkylene oxide may be employed, e.g., propylene oxide, in which case the product is a homopolymer, e.g., a poly(oxypropylene). However, copolymers are equally satisfactory and random copolymers are readily prepared by contacting the metal salt VI with a mixture of alkylene oxides, such as a mixture of propylene oxide and 1,2-butylene oxide, under polymerization conditions. Copolymers containing blocks of oxyalkylene units are also suitable for use in the present invention. Block copolymers may be prepared by contacting the metal salt VI with first one alkylene oxide, then others in any order, or repetitively, under polymerization conditions.

The poly(oxyalkylene) alcohol V may also be prepared by living or immortal polymerization as described by S. Inoue and T. Aida in Encyclopedia of Polymer Science and Engineering, Second Edition, Supplemental Volume, J. Wiley and Sons, New York, pages 412–420 (1989). These procedures are especially useful for preparing poly(oxyalkylene) alcohols of formula V in which $R_3$ and $R_4$ are both alkyl groups.

As noted above, the alkoxide or phenoxide metal salt VI is generally derived from the corresponding hydroxy compound, $R_{12}OH$. Preferred hydroxy compounds for use in this invention include straight- or branched-chain aliphatic alcohols having 1 to about 30 carbon atoms and phenols having the formula:

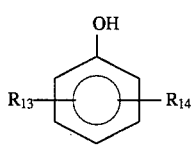

(VIII)

wherein $R_{13}$ and $R_{14}$ are each independently hydrogen or an alkyl group having 1 to about 30 carbon atoms.

Preferably, the straight- or branched-chain aliphatic alcohols employed in this invention will contain 2 to about 22 carbon atoms, more preferably 4 to 12 carbon atoms. Representative examples of straight- or branched-chain aliphatic alcohols suitable for use in this invention include, but are not limited to, n-butanol; isobutanol; sec-butanol; t-butanol; n-pentanol; n-hexanol; n-heptanol; n-octanol; isooctanol; n-nonanol; n-decanol; n-dodecanol; n-hexadecanol (cetyl alcohol); n-octadecanol (stearyl alcohol); alcohols derived from linear $C_{10}$ to $C_{30}$ alpha olefins and mixtures thereof; and alcohols derived from polymers of $C_2$ to $C_6$ olefins, such as alcohols derived from polypropylene and polybutene, including polypropylene alcohols having 9 to about 30 carbon atoms. Particularly preferred aliphatic alcohols are butanols.

The alkylphenols of formula VIII used in this invention may be monoalkyl-substituted phenols or dialkyl-substituted phenols. Monoalkyl-substituted phenols are preferred, especially monoalkylphenols having an alkyl substituent in the para position.

Preferably, the alkyl group of the alkylphenols employed in this invention will contain 4 to about 24 carbon atoms, more preferably 4 to 12 carbon atoms. Representative examples of phenols suitable for use in this invention include, phenol, methylphenol, dimethylphenol, ethylphenol, butylphenol, octylphenol, decylphenol, dodecylphenol, tetradecylphenol, hexadecylphenol, octadecylphenol, eicosylphenol, tetracosylphenol, hexacosylphenol, triacontylphenol and the like. Also, mixtures of alkylphenols may be employed, such as a mixture of $C_{14}$–$C_{18}$ alkylphenols, a mixture of $C_{18}$–$C_{24}$ alkylphenols, a mixture of $C_{20}$–$C_{24}$ alkylphenols, or a mixture of $C_{16}$–$C_{26}$ alkylphenols.

Particularly preferred alkylphenols are those derived from alkylation of phenol with polymers or oligomers of $C_3$ to $C_6$ olefins, such as polypropylene or polybutene. These polymers preferably contain 10 to 30 carbon atoms. An especially preferred alkylphenol is prepared by alkylating phenol with a propylene polymer having an average of 4 units. This polymer has the common name of propylene tetramer and is commercially available.

As indicated above, the poly(oxyalkylene) hydroxyaromatic esters of formula III may be prepared by esterifying a hydroxyaromatic carboxylic acid of formula IV with a poly(oxyalkylene) alcohol of formula V under conventional esterification reaction conditions.

Typically, this reaction will be conducted by contacting a poly(oxyalkylene) alcohol of formula V with about 0.25 to about 1.5 molar equivalents of a hydroxyaromatic carboxylic acid of formula IV in the presence of acidic catalyst at a temperature in the range of 70° C. to about 160° C. for about 0.5 to about 48 hours. Suitable acid catalysts for this reaction include p-toluenesulfonic acid, methanesulfonic acid and the like. The reaction may be conducted in the presence or absence of an inert solvent, such as benzene, toluene and the like. The water generated by this reaction is preferably removed during the course of the reaction by, for example, azeotropic distillation with an inert solvent, such as toluene.

The poly(oxyalkylene) hydroxyaromatic esters of formula III may also be synthesized by reacting a poly(oxyalkylene) alcohol of formula V with an acyl halide having the formula:

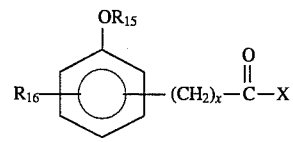

(IX)

wherein X is a halide, such as chloride or bromide, and $R_{15}$ is a suitable hydroxyl protecting group, such as benzyl, tert-butyldimethylsilyl, methoxymethyl, and the like; $R_{16}$ is hydrogen, lower alkyl, lower alkoxy, or the group —$OR_{18}$, wherein $R_{18}$ is a suitable hydroxyl protecting group.

Acyl halides of formula IX may be prepared from hydroxyaromatic carboxylic acids of formula IV by first protecting the aromatic hydroxyl groups of IV to form a carboxylic acid having the formula:

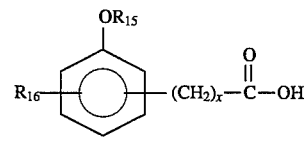

(X)

wherein $R_{15}$, $R_{16}$ and x are as defined above, and then converting the carboxylic acid moiety of X into an acyl halide using conventional procedures.

Protection of the aromatic hydroxyl groups of IV may be accomplished using well known procedures. The choice of a suitable protecting group for a particular hydroxyaromatic carboxylic acid will be apparent to those skilled in the art. Various protecting groups, and their introduction and removal, are described, for example, in T. W. Greene and P. G. M. Wuts, Protective Groups in Organic Synthesis, Second Edition, Wiley, New York, 1991, and references cited therein. Alternatively, the protected derivatives X can be prepared from known starting materials other than the hydroxyaromatic compounds of formula IV by conventional procedures.

The carboxylic acid moiety of X may be converted into an acyl halide by contacting X with an inorganic acid halide, such as thionyl chloride, phosphorous trichloride, phosphorous tribromide, or phosphorous pentachloride; or alternatively, with oxalyl chloride. Generally, this reaction will be conducted using about 1 to 5 molar equivalents of the inorganic acid halide or oxalyl chloride, either neat or in an inert solvent, such as diethyl ether, at a temperature in the range of about 20° C. to about 80° C. for about 1 to about 48 hours. A catalyst, such as N,N-dimethylformamide, may also be used in this reaction.

In certain cases where the hydroxyaromatic carboxylic acids of formula IV having bulky alkyl groups adjacent to the hydroxyl group, such as 3,5-di-t-butyl-4-hydroxybenzoic acid, it will generally not be necessary to protect the hydroxyl group prior to formation of the acyl halide, since such hydroxyl groups are sufficiently sterically hindered so as to be substantially non-reactive with the acyl halide moiety.

Reaction of acyl halide IX with poly(oxyalkylene) alcohol V provides an intermediate poly(oxyalkylene) ester having the formula:

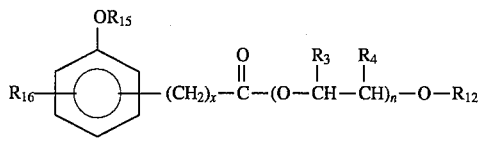
(XI)

wherein $R_3$, $R_4$, $R_{12}$, $R_{15}$, $R_{16}$, n and x are as defined above.

Typically, this reaction is conducted by contacting V with about 0.9 to about 1.5 molar equivalents of IX in an inert solvent, such as toluene, dichloromethane, diethyl ether, and the like, at a temperature in the range of about 25° C. to about 150° C. The reaction is generally complete in about 0.5 to about 48 hours. Preferably, the reaction is conducted in the presence of a sufficient amount of an amine capable of neutralizing the acid generated during the reaction, such as triethylamine, di(isopropyl)ethylamine, pyridine or 4-dimethylamino pyridine.

Deprotection of the aromatic hydroxyl group(s) of XI then provides a poly(oxyalkylene) hydroxyaromatic ester of formula III. Appropriate conditions for this deprotection step will depend upon the protecting group(s) utilized in the synthesis and will be readily apparent to those skilled in the art. For example, benzyl protecting groups may be removed by hydrogenolysis under 1 to about 4 atmospheres of hydrogen in the presence of a catalyst, such as palladium on carbon. Typically, this deprotection reaction is conducted in an inert solvent, preferably a mixture of ethyl acetate and acetic acid, at a temperature of from about 0° C. to about 40° C. for about 1 to about 24 hours.

The poly(oxyalkylene) hydroxyaromatic esters of formula A having the formula:

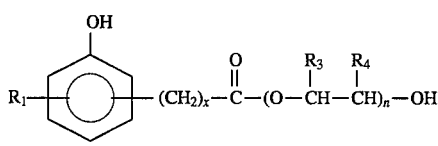
(XII)

wherein $R_1$, $R_3$, $R_4$, n and x are as defined above, can be prepared from compounds of formula III or XI, wherein $R_{12}$ is a benzyl group, by removing the benzyl group using conventional hydrogenolysis procedures. Compounds of formula III or XI where $R_{12}$ represents a benzyl group may be prepared by employing a metal salt VI derived from benzyl alcohol in the above-described synthetic procedures.

Similarly, the poly(oxyalkylene) hydroxyaromatic esters of formula A having the formula:

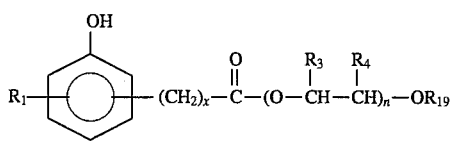
(XIII)

wherein $R_1$, $R_3$, $R_4$, n and x are as defined above and $R_{19}$ is an acyl group having the formula:

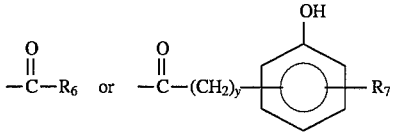

wherein $R_6$, $R_7$ and y are as defined above, can be synthesized in several steps from a compound of formula XI, wherein $R_{12}$ represents a benzyl group and $R_{15}$ (and optionally $R_{18}$) represents a hydroxyl protecting group that is stable to hydrogenolysis conditions, such as a tert-butyldimethyl-silyl group. The synthesis of XIII from such compounds may be effected by first removing the benzyl group using conventional hydrogenolysis conditions and then acylating the resulting hydroxyl group with a suitable acylating agent. Removal of the protecting group(s) from the aromatic hydroxyl group(s) using conventional procedures then provides a poly(oxyalkylene) hydroxyaromatic ester of formula XIII.

Suitable acylating agents for use in this reaction include acyl halides, such as acyl chlorides and bromides; and carboxylic acid anhydrides. Preferred acylating agents are those having the formula: $R_6C(O)$—X, wherein $R_6$ is alkyl having 1 to 30 carbon atom, phenyl, or aralkyl or alkaryl having 7 to 36 carbon atoms, and X is chloro or bromo; and those having the formula:

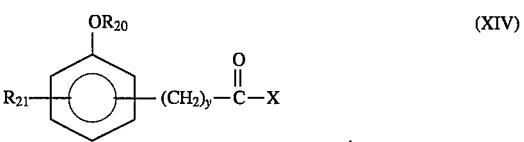
(XIV)

wherein X is a halide, such as chloride or bromide, $R_{20}$ is a suitable hydroxyl protecting group, $R_{21}$ is hydrogen, lower alkyl, lower alkoxy, or the group —$OR_{23}$, wherein $R_{23}$ is a suitable hydroxyl protecting group, and y is an integer from 0 to 10.

A particularly preferred group of acylating agents are those having the formula: $R_{24}C(O)$—X, wherein $R_{24}$ is alkyl having 4 to 12 carbon atoms. Representative examples of such acylating agents include acetyl chloride, propionyl chloride, butanoyl chloride, pivaloyl chloride, octanoyl chloride, decanoyl chloride and the like.

Another particularly preferred group of acylating agents are those of formula XIV, wherein $R_{20}$ is benzyl; $R_{21}$ is hydrogen, alkyl having 1 to 4 carbon atoms, or —$OR_{25}$, wherein $R_{25}$ is a suitable hydroxyl protecting group, preferably benzyl; and y is 0, 1 or 2. Representative examples of such acylating agents include 4-benzyloxybenzoyl chloride, 3-benzyloxybenzoyl chloride, 4-benzyloxy-3-methylbenzoyl chloride, 4-benzyloxyphenylacetyl chloride, 3-(4-benzyloxyphenyl)propionyl chloride, and the like.

Generally, this acylation reaction will be conducted using about 0.95 to about 1.2 molar equivalents of the acylating agent. The reaction is typically conducted in an inert solvent, such as toluene, dichloromethane, diethyl ether and the like, at a temperature in the range of about 25° C. to about 150° C. for about 0.5 to about 48 hours. When an acyl halide is employed as the acylating agent, the reaction is preferably conducted in the presence of a sufficient amount of an amine capable of neutralizing the acid generated during the reaction, such as triethylamine, di(isopropyl)-ethylamine, pyridine or 4-dimethylaminopyridine.

A particularly preferred group of poly(oxyalkylene) hydroxyaromatic esters of formula XIII are those having the same hydroxyaromatic ester group at each end the poly(oxyalkylene) moiety, i.e., compounds of formula XIII wherein $R_{19}$ is an acyl group having the formula:

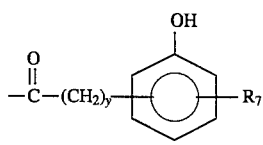

wherein $R_7$ is the same group as $R_1$, and x and y are the same integer.

These compounds may be prepared from a poly(oxyalkylene) diol having the formula:

wherein $R_3$, $R_4$, and n are as defined above, by esterifying each of the hydroxyl groups present in XV with a hydroxyaromatic carboxylic acid of formula IV or an acyl halide of formula IX using the above described synthetic procedures. The poly(oxyalkylene) diols of formula XV are commercially available or may be prepared by conventional procedures, for example, by using sodium or potassium hydroxide in place of the alkoxide or phenoxide metal salt VI in the above described alkylene oxide polymerization reaction.

Those skilled in the art will recognize that it may be necessary to block or protect certain functional groups while conducting the present synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, Protective Groups in Organic Synthesis, Second Edition, Wiley, New York, 1991, and references cited therein.

In the present synthetic procedures, a hydroxyl group will preferably be protected, when necessary, as the benzyl or tert-butyldimethylsilyl ether. Introduction and removal of these protecting groups is well described in the art.

The products or product mixtures can be recovered from the respective reaction product mixtures by any suitable separation and purification procedure, such as, for example, extraction, evaporation, and recrystallization. Suitable separation and purification procedures for recovering product mixtures are, for example, illustrated in the examples set forth hereinbelow.

Fuel Compositions

The compounds of the present invention are useful as additives in hydrocarbon fuels to prevent and control engine deposits, particularly intake valve deposits. The proper concentration of additive necessary to achieve the desired deposit control varies depending upon the type of fuel employed, the type of engine, and the presence of other fuel additives.

In general, the concentration of the Mannich condensation products of this invention in hydrocarbon fuel will range from about 50 to about 2500 parts per million (ppm) by weight, preferably from 75 to 1000 ppm. When other deposit control additives are present, a lesser amount of the present additive may be used.

The Mannich condensation products of the present invention may be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will generally range from about 10 to about 70 weight percent, preferably 10 to 50 weight percent, more preferably from 20 to 40 weight percent.

In gasoline fuels, other fuel additives may be employed with the additives of the present invention, including, for example, oxygenares, such as t-butyl methyl ether, antiknock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators and demulsifiers may be present. The gasoline fuels may also contain amounts of other fuels such as, for example, methanol.

In diesel fuels, other well-known additives can be employed, such as pour point depressants, flow improvers, cetane improvers, and the like. The diesel fuels can also include other fuels such as, for example, methanol.

A fuel-soluble, nonvolatile carrier fluid or oil may also be used with the Mannich condensation products of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, and synthetic polyoxyalkylene-derived oils, such as those described, for example, in U.S. Pat. No. 4,191,537 to Lewis, and polyesters, such as those described, for example, in U.S. Pat. Nos. 3,756,793 and 5,004,478 to Robinson and Vogel et al., respectively, and in European Patent Application Nos. 356,726 and 382,159, published Mar. 7, 1990 and Aug. 16, 1990, respectively.

These carrier fluids are believed to act as a carrier for the fuel additives of the present invention and to assist in removing and retarding deposits. The carrier fluid may also exhibit synergistic deposit control properties when used in combination with a Mannich condensation product of this invention.

The carrier fluids are typically employed in amounts ranging from about 100 to about 5000 ppm by weight of the hydrocarbon fuel, preferably from 400 to 3000 ppm of the fuel. Preferably, the ratio of carrier fluid to deposit control additive will range from about 0.5:1 to about 10:1, more preferably from 1:1 to 4:1, most preferably about 2:1.

When employed in a fuel concentrate, carrier fluids will generally be present in amounts ranging from about 20 to about 60 weight percent, preferably from 30 to 50 weight percent.

PREPARATIONS AND EXAMPLES

A further understanding of the invention can be had in the following nonlimiting examples. Unless expressly stated to the contrary, all temperatures and temperature ranges refer to the Centigrade system and the term "ambient" or "room temperature" refers to about 20° C.–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 300 mHz, signals are assigned as singlets (s), broad singlets (bs), doublets (d), double doublets (dd), triplets (t), double triplets (dt), quartets (q), and multiplets (m), and cps refers to cycles per second.

EXAMPLE 1

Preparation of 4-Benzyloxybenzoyl Chloride

To a flask equipped with a magnetic stirrer and drying tube was added 10.0 grams of 4-benzyloxybenzoic acid and 100 mL of anhydrous diethyl ether and then 19.1 mL of oxalyl chloride. The resulting mixture was stirred at room temperature for 16 hours and then the solvent was removed in vacuo to yield 10.8 grams of the desired acid chloride.

EXAMPLE 2

Preparation of α-(4-Benzyloxybenzoyl)-ω-4-dodecylphenoxypoly(oxybutylene)

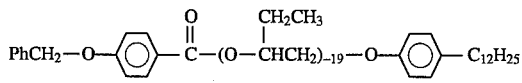

4-benzyloxybenzoyl chloride (10.8 grams) from Example 1 was combined with 72.2 grams of α-hydroxy-ω-4-dodecylphenoxy-poly(oxybutylene) having an average of 19 oxybutylene units (prepared essentially as described in Example 6 of U.S. Pat. No. 4,160,648) and 150 mL of anhydrous toluene. Triethylamine (6.41 mL) and 4-dimethylaminopyridine (0.54 grams) were then added and the resulting mixture was heated to reflux under nitrogen for 16 hours. The reaction was then cooled to room temperature and diluted with 300 mL of diethyl ether. The organic layer was washed twice with 1% aqueous hydrochloric acid, twice with saturated aqueous sodium bicarbonate solution, and once with saturated aqueous sodium chloride. The organic layer was then dried over anhydrous magnesium sulfate, filtered and the solvents removed in vacuo to yield 76.5 grams of a light brown oil. The oil was chromatographed on silica gel, eluting with hexane/diethyl ether/ethanol (8:1.5:0.5), to yield 43.2 grams of the desired product as a colorless oil.

EXAMPLE 3

Preparation of α-(4-Hydroxybenzoyl)-ω-4-dodecylphenoxypoly(oxybutylene)

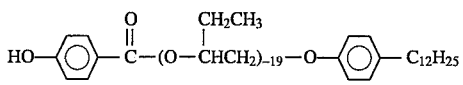

A solution of 15.9 grams of the product from Example 2 in 50 mL of ethyl acetate and 50 mL of acetic acid containing 3.48 grams of 5% palladium on charcoal was hydrogenolyzed at 35–40 psi for 16 hours on a Parr low-pressure hydrogenator. Catalyst filtration and removal of residual acetic acid with toluene in vacuo yielded 14.6 grams of the desired product as a colorless oil. The product had an average of 19 oxybutylene units. IR (neat) 1715 cm$^{-1}$; $^1$H NMR (CDCl$_3$) δ 7.9, 7.3 (AB quartet, 4H), 7.1–7.25 (m, 2H), 6.7–6.9 (m, 2H), 5.05–5.15 (m, 1H), 3.1–4.0 (m, 56H), 0.5–1.9 (m, 120H).

EXAMPLE 4

Preparation of α-(3-Hydroxybenzoyl)-ω-4-dodecylphenoxypoly(oxybutylene)

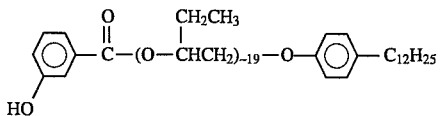

To a flask equipped with a magnetic stirrer, thermometer, Dean-Stark trap, nitrogen inlet and reflux condenser was added 5.08 grams of 3-hydroxybenzoic acid, 50.0 grams of α-hydroxy-ω-4-dodecylphenoxy-poly(oxybutylene) having an average of 19 oxybutylene units (prepared essentially as described in Example 6 of U.S. Pat. No. 4,160,648) and 0.53 grams of p-toluenesulfonic acid. The reaction was heated to 130° C. for 48 hours and then cooled to room temperature. Diethyl ether (750 mL) was added and the organic phase was washed twice with saturated aqueous sodium bicarbonate and once with saturated aqueous sodium chloride solution. The organic layer was then dried over anhydrous magnesium sulfate, filtered and concentrated in vacuo to afford 47.8 grams of a brown oil. The oil was chromatographed on silica gel, eluting with hexane/ethyl acetate/ethanol (78:20:2) to yield 16.5 grams of the desired product as a yellow oil. The product had an average of 19 oxybutylene groups. IR (neat) 1716 cm$^{-1}$; $^1$H NMR (CDCl$_3$) δ 6.6–7.6 (m, 8H), 4.9–5.2 (m, 1H), 3.1–4.0 (m, 56H), 0.5–1.9 (m, 21H).

EXAMPLE 5

Mannich Condensation Product of α-(4-Hydroxybenzoyl)-ω-4-dodecylphenoxvpoly(oxybutylene)

To a flask equipped with a magnetic stirrer, thermometer, reflux condensor and nitrogen inlet was added the product as prepared in Example 3 (50.0 grams) and diethylene triamine (3.1 mL). The mixture was heated to 90° C. and formaldehyde (2.3 mL of a 37 weight percent solution in water) was added. The reaction was heated for sixteen hours at 90° C.

and the temperature was then raised to 135° C. The reaction was maintained at 135° C. for two hours while sweeping out the water with a stream of nitrogen. The reaction was cooled to room temperature and yielded a brown oil. The oil was chromatographed on silica gel eluting with hexane/diethyl ether (1:1), followed by hexane/diethyl ether/methanol/iso propylamine (4:4:1.5:0.5) to yield 7.7 grams of the desired product as a brown-red oil. $^1$H NMR (CDCl$_3$, D$_2$O) δ7.70–8.05 (m, 2H), 7.15–7.35 (m, 2H), 6.7–7.0 (m, 3H), 5.1–5.25 (m, 1H), 2.2–4.05 (m, 66H), 0.6–1.9 (m, 120H).

EXAMPLE 6

Mannich Condensation Product of α-(3-Hydroxybenzoyl)-ω-4-dodecylphenoxypoly(oxybutylene)

To a flask equipped with a magnetic stirrer, thermometer, reflux condensor and nitrogen inlet was added the product as prepared in Example 4 (6.9 grams) and diethylene triamine (0.5 mL). The mixture was heated to 90° C. and formaldehyde (0.9 mL of a 37 weight percent solution in water) was added. The reaction was heated for sixteen hours at 90° C. and the temperature was then raised to 135° C. The reaction was maintained at 135° C. for two hours while sweeping out the water with a stream of nitrogen. The reaction was cooled to room temperature and yielded a brown oil. The oil was chromatographed on silica gel eluting with hexane/diethyl ether (1:1), followed by hexane/diethyl ether/methanol/iso propylamine (4:4:1.5:0.5) to yield 1.1 grams of the desired product as a yellow-brown oil. $^1$H NMR (CDCl$_3$, D$_2$O) δ 7.45–7.6 (m, 1H), 6.95–7.3 (m, 4H), 6.75–6.9 (m, 2H), 5.05–5.2 (m, 1H), 2.2–4.05 (m, 66H), 0.6–1.9 (m, 120H).

EXAMPLE 7

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 40° BTC; engine speed is 1800 rpm; the crankcase oil is a commercial 30W oil.

The amount of carbonaceous deposit in milligrams on the intake valves is reported for each of the test compounds in Table I. (Reference to a compound by Example No. refers to the title composition for that Example.)

TABLE I

| Sample[1] | Intake Valve Deposit Weight (in milligrams) | | |
|---|---|---|---|
| | Run 1 | Run 2 | Average |
| Base Fuel | 198.1 | 180.4 | 189.3 |
| Example 5 | 23.7 | 28.3 | 26.0 |

[1]At 200 parts per million actives (ppma).

TABLE II

| Sample[1] | Intake Valve Deposit Weight (in milligrams) | | |
|---|---|---|---|
| | Run 1 | Run 2 | Average |
| Base Fuel | 254.9 | 303.2 | 279.1 |
| Example 6 | 27.0 | 17.6 | 22.3 |

[1]At 150 parts per million actives (ppma).

The base fuel employed in the above single-cylinder engine tests was a regular octane unleaded gasoline containing no fuel detergent. The test compounds were admixed with the base fuel to give a concentration of 200 ppma (parts per million actives) or 150 ppma.

The data in Tables I and II illustrates the outstanding reduction in intake valve deposits provided by the Mannich condensation product of the present fuel additive composition compared to the base fuel.

Obviously, many modifications and variations of the invention described hereinabove and below can be made without departing from the essence and scope thereof.

What is claimed is:

1. A composition prepared by the Mannich condensation of a compound of the formula:

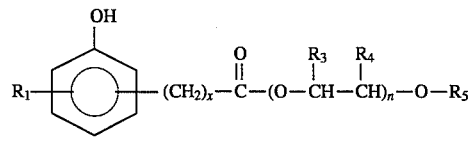

wherein R$_1$ is hydrogen, hydroxy, lower alkyl having 1 to 6 carbon atoms, or lower alkoxy having 1 to 6 carbon atoms;

R$_3$ and R$_4$ are each independently hydrogen or lower alkyl having 1 to 6 carbon atoms;

R$_5$ is hydrogen, alkyl having 1 to 30 carbon atoms, phenyl, aralkyl or alkaryl having 7 to 36 carbon atoms, or an acyl group having the formula:

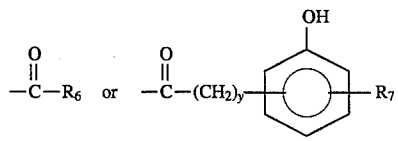

wherein R$_6$ is alkyl having 1 to 30 carbon atoms, phenyl, or aralkyl or alkaryl having 7 to 36 carbon atoms;

R$_7$ is hydrogen, hydroxy, lower alkyl having 1 to 6 carbon atoms, or lower alkoxy having 1 to 6 carbon atoms;

n is an integer from 5 to 100; and x and y are each independently an integer from 0 to 10;

with an aldehyde having the formula HR$_2$C(O), wherein R$_2$ is hydrogen or lower alkyl having 1 to 6 carbon atoms, and a nitrogen base selected from ammonia, lower alkylamine having 1 to 6 carbon atoms, a polyamine having 2 to about 12 amine nitrogen atoms and 2 to about 40 carbon atoms and mixtures thereof.

2. The composition according to claim 1, wherein n is an integer ranging from 10 to 50.

3. The composition according to claim 2, wherein n is an integer ranging from 15 to 30.

4. The composition according to claim 2, wherein R$_1$ is hydrogen, hydroxy, or lower alkyl having 1 to 4 carbon atoms; and said nitrogen base is a polyalkylene polyamine.

5. The composition according to claim 4, wherein $R_5$ is hydrogen, alkyl having 2 to 22 carbon atoms, or alkylphenyl having an alkyl group containing 4 to 24 carbon atoms.

6. The composition according to claim 5, wherein $R_1$ is hydrogen or hydroxy, and said nitrogen base is a polyethylene polyamine or a polypropylene polyamine.

7. The composition according to claim 6, wherein $R_5$ is hydrogen, alkyl having 4 to 12 carbon atoms, or alkylphenyl having an alkyl group containing 4 to 12 carbon atoms.

8. The composition according to claim 7, wherein one of $R_3$ and $R_4$ is lower alkyl having 1 to 3 carbon atoms and the other is hydrogen.

9. The composition according to claim 8, wherein one of $R_3$ and $R_4$ is methyl or ethyl and the other is hydrogen.

10. The composition according to claim 9, wherein x is 0, 1 or 2.

11. The composition according to claim 10, wherein $R_1$ is hydrogen, $R_5$ is alkylphenyl having an alkyl group containing 4 to 12 carbon atoms, x is 0, and said nitrogen base is ethylene diamine or diethylene triamine.

12. A compound of the formula:

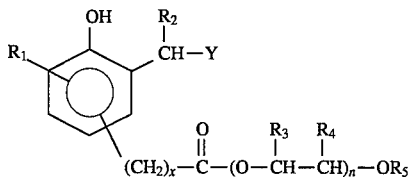

wherein $R_1$ is hydrogen, hydroxy, lower alkyl having 1 to 6 carbon atoms, or lower alkoxy having 1 to 6 carbon atoms;

$R_2$ is hydrogen or lower alkyl having 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

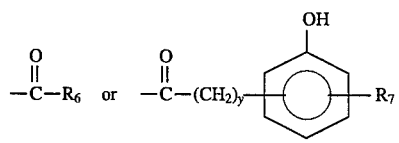

wherein $R_6$ is alkyl having 1 to 30 carbon atoms, phenyl, or aralkyl or alkaryl having 7 to 36 carbon atoms;

$R_7$ is hydrogen, hydroxy, lower alkyl having 1 to 6 carbon atoms, or lower alkoxy having 1 to 6 carbon atoms;

n is an integer from 5 to 100; and x and y are each independently an integer from 0 to 10; and Y is selected from amino, lower alkylamino having 1 through 6 carbon atoms or a polyamine radical having 2 through 12 amine nitrogen atoms and 2 through 40 carbon atoms; wherein the attachment of Y to the —$CHR_2$— linking group is through one of its amine nitrogen atoms.

13. The compound according to claim 12, wherein n is an integer ranging from 10 to 50.

14. The compound according to claim 13, wherein n is an integer ranging from 15 to 30.

15. The compound according to claim 13, wherein $R_1$ is hydrogen, hydroxy, or lower alkyl having 1 to 4 carbon atoms; and Y is a polyalkylene polyamine radical.

16. The compound according to claim 15, wherein $R_5$ is hydrogen, alkyl having 2 to 22 carbon atoms, or alkylphenyl having an alkyl group containing 4 to 24 carbon atoms.

17. The compound according to claim 16, wherein $R_1$ is hydrogen or hydroxy, and Y is a polyethylene polyamine radical or a polypropylene polyamine radical.

18. The compound according to claim 17, wherein $R_5$ is hydrogen, alkyl having 4 to 12 carbon atoms, or alkylphenyl having an alkyl group containing 4 to 12 carbon atoms.

19. The compound according to claim 18, wherein one of $R_3$ and $R_4$ is lower alkyl having 1 to 3 carbon atoms and the other is hydrogen.

20. The compound according to claim 19, wherein one of $R_3$ and $R_4$ is methyl or ethyl and the other is hydrogen.

21. The compound according to claim 20, wherein x is 0, 1 or 2.

22. The compound according to claim 21, wherein $R_1$ is hydrogen, $R_5$ is alkylphenyl having an alkyl group containing 4 to 12 carbon atoms, x is 0, and Y is an ethylene diamine radical or a diethylene triamine radical.

23. A fuel composition comprising a major amount of hydrocarbons boiling in the gasoline or diesel range and an effective deposit-controlling amount of a composition prepared by the Mannich condensation of a compound of the formula:

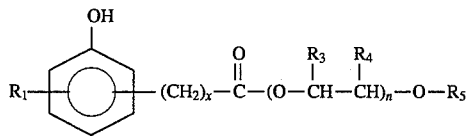

wherein $R_1$ is hydrogen, hydroxy, lower alkyl having 1 to 6 carbon atoms, or lower alkoxy having 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

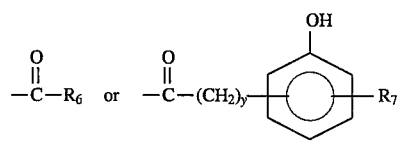

wherein $R_6$ is alkyl having 1 to 30 carbon atoms, phenyl, or aralkyl or alkaryl having 7 to 36 carbon atoms;

$R_7$ is hydrogen, hydroxy, lower alkyl having 1 to 6 carbon atoms, or lower alkoxy having 1 to 6 carbon atoms;

n is an integer from 5 to 100; and x and y are each independently an integer from 0 to 10;

with an aldehyde having the formula $HR_2C(O)$, wherein $R_2$ is hydrogen or lower alkyl having 1 to 6 carbon atoms, and a nitrogen base selected from ammonia, lower alkylamine having 1 to 6 carbon atoms, a polyamine having 2 to about 12 amine nitrogen atoms and 2 to about 40 carbon atoms and mixtures thereof.

24. The fuel composition according to claim 23, wherein $R_1$ is hydrogen, hydroxy, or lower alkyl having 1 to 4 carbon atoms; one of $R_3$ and $R_4$ is hydrogen and the other is methyl or ethyl; $R_5$ is hydrogen, alkyl having 2 to 22 carbon atoms, or alkylphenyl having an alkyl group containing 4 to 24 carbon atoms; n is 15 to 30; x is 0, 1 or 2; and said nitrogen base is a polyalkylene polyamine.

25. The fuel composition according to claim 24, wherein $R_1$ is hydrogen or hydroxy; $R_5$ is hydrogen, alkyl having 4 to 12 carbon atoms, or alkylphenyl having an alkyl group containing 4 to 12 carbon atoms; x is 0; and said nitrogen base is a polyethylene polyamine or a polypropylene polyamine.

26. The fuel composition according to claim 25, wherein $R_1$ is hydrogen, $R_5$ is alkylphenyl having an alkyl group containing 4 to 12 carbon atoms, and said nitrogen base is ethylene diamine or diethylene triamine.

27. A fuel composition comprising a major amount of hydrocarbons boiling in the gasoline or diesel range and an effective deposit-controlling amount of a compound of the formula:

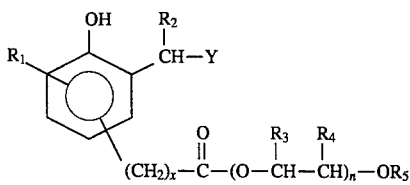

wherein $R_1$ is hydrogen, hydroxy, lower alkyl having 1 to 6 carbon atoms, or lower alkoxy having 1 to 6 carbon atoms;

$R_2$ is hydrogen or lower alkyl having 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

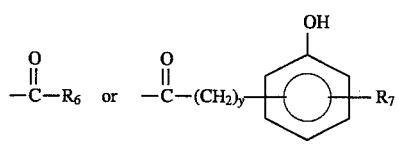

wherein $R_6$ is alkyl having 1 to 30 carbon atoms, phenyl, or aralkyl or alkaryl having 7 to 36 carbon atoms;

$R_7$ is hydrogen, hydroxy, lower alkyl having 1 to 6 carbon atoms, or lower alkoxy having 1 to 6 carbon atoms;

n is an integer from 5 to 100; and x and y are each independently an integer from 0 to 10; and Y is selected from amino, lower alkylamino having 1 through 6 carbon atoms or a polyamine radical having 2 through 12 amine nitrogen atoms and 2 through 40 carbon atoms; wherein the attachment of Y to the —$CHR_2$— linking group is through one of its amine nitrogen atoms.

28. The fuel composition according to claim 27, wherein $R_1$ is hydrogen, hydroxy, or lower alkyl having 1 to 4 carbon atoms; one of $R_3$ and $R_4$ is hydrogen and the other is methyl or ethyl; $R_5$ is hydrogen, alkyl having 2 to 22 carbon atoms, or alkylphenyl having an alkyl group containing 4 to 24 carbon atoms; n is 15 to 30; x is 0, 1 or 2; and Y is a polyalkylene polyamine radical.

29. The fuel composition according to claim 28, wherein $R_1$ is hydrogen or hydroxy; $R_5$ is hydrogen, alkyl having 4 to 12 carbon atoms, or alkylphenyl having an alkyl group containing 4 to 12 carbon atoms; x is 0; and Y is a polyalkylene polyamine radical.

30. The fuel composition according to claim 29, wherein $R_1$ is hydrogen, $R_5$ is alkylphenyl having an alkyl group containing 4 to 12 carbon atoms, and Y is an ethylene diamine radical or a diethylene triamine radical.

31. A fuel concentrate comprising an inert stable oleophilic organic solvent boiling in the range of from about 150° F. to 400° F. and from about 10 to about 70 weight percent of a composition prepared by the Mannich condensation of a compound of the formula:

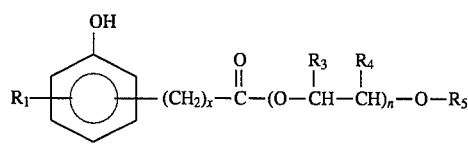

wherein $R_1$ is hydrogen, hydroxy, lower alkyl having 1 to 6 carbon atoms, or lower alkoxy having 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

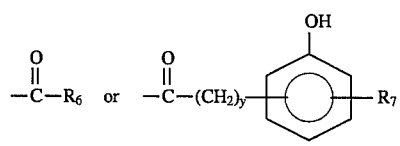

wherein $R_6$ is alkyl having 1 to 30 carbon atoms, phenyl, or aralkyl or alkaryl having 7 to 36 carbon atoms;

$R_7$ is hydrogen, hydroxy, lower alkyl having 1 to 6 carbon atoms, or lower alkoxy having 1 to 6 carbon atoms;

n is an integer from 5 to 100; and x and y are each independently an integer from 0 to 10;

with an aldehyde having the formula $HR_2C(O)$, wherein $R_2$ is hydrogen or lower alkyl having 1 to 6 carbon atoms, and a nitrogen base selected from ammonia, lower alkylamine having 1 to 6 carbon atoms, a polyamine having 2 to about 12 amine nitrogen atoms and 2 to about 40 carbon atoms and mixtures thereof.

32. The fuel concentrate according to claim 31, wherein $R_1$ is hydrogen, hydroxy, or lower alkyl having 1 to 4 carbon atoms; one of $R_3$ and $R_4$ is hydrogen and the other is methyl or ethyl; $R_5$ is hydrogen, alkyl having 2 to 22 carbon atoms, or alkylphenyl having an alkyl group containing 4 to 24 carbon atoms; n is 15 to 30; x is 0, 1 or 2; and said nitrogen base is a polyalkylene polyamine.

33. The fuel concentrate according to claim 32, wherein $R_1$ is hydrogen or hydroxy; $R_5$ is hydrogen, alkyl having 4 to 12 carbon atoms, or alkylphenyl having an alkyl group containing 4 to 12 carbon atoms; x is 0; and said nitrogen base is a polyethylene polyamine or a polypropylene polyamine.

34. The fuel concentrate according to claim 33, wherein $R_1$ is hydrogen, $R_5$ is alkylphenyl having an alkyl group containing 4 to 12 carbon atoms, and said nitrogen base is ethylene diamine or diethylene triamine.

35. A fuel concentrate comprising an inert stable oleophilic organic solvent boiling in the range of from about 150° F. to 400° F. and from about 10 to about 70 weight percent of a compound of the formula:

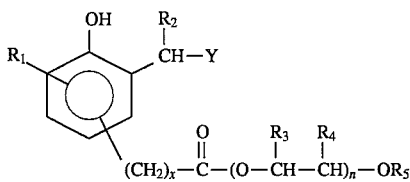

wherein $R_1$ is hydrogen, hydroxy, lower alkyl having 1 to 6 carbon atoms, or lower alkoxy having 1 to 6 carbon atoms;

$R_2$ is hydrogen or lower alkyl having 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

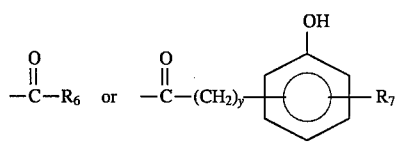

wherein $R_6$ is alkyl having 1 to 30 carbon atoms, phenyl, or aralkyl or alkaryl having 7 to 36 carbon atoms;

$R_7$ is hydrogen, hydroxy, lower alkyl having 1 to 6 carbon atoms, or lower alkoxy having 1 to 6 carbon atoms;

n is an integer from 5 to 100; and x and y are each independently an integer from 0 to 10; and Y is selected from amino, lower alkylamino having 1 through 6 carbon atoms or a polyamine radical having 2 through 12 amine nitrogen atoms and 2 through 40 carbon atoms; wherein the attachment of Y to the —$CHR_2$— linking group is through one of its amine nitrogen atoms.

36. The fuel concentrate according to claim 35, wherein $R_1$ is hydrogen, hydroxy, or lower alkyl having 1 to 4 carbon atoms; one of $R_3$ and $R_4$ is hydrogen and the other is methyl or ethyl; $R_5$ is hydrogen, alkyl having 2 to 22 carbon atoms, or alkylphenyl having an alkyl group containing 4 to 24 carbon atoms; n is 15 to 30; x is 0, 1 or 2; and Y is a polyalkylene polyamine radical.

37. The fuel concentrate according to claim 36, wherein $R_1$ is hydrogen or hydroxy; $R_5$ is hydrogen, alkyl having 4 to 12 carbon atoms, or alkylphenyl having an alkyl group containing 4 to 12 carbon atoms; x is 0; and Y is a polyethylene polyamine radical or a polypropylene polyamine radical.

38. The fuel concentrate according to claim 37, wherein $R_1$ is hydrogen, $R_5$ is alkylphenyl having an alkyl group containing 4 to 12 carbon atoms, and Y is an ethylene diamine radical or a diethylene triamine radical.

* * * * *